(12) United States Patent
Koch et al.

(10) Patent No.: US 8,921,617 B2
(45) Date of Patent: Dec. 30, 2014

(54) METHOD FOR PRODUCING 1,2-PENTANEDIOL

(75) Inventors: Oskar Koch, Göttingen (DE); Angela Köckritz, Berlin (DE); Michael Kant, Berlin (DE); Andreas Martin, Berlin (DE); Axel Schöning, Holzminden (DE); Udo Armbruster, Rostok (DE); Michael Bartoszek, Berlin (DE); Sigrid Evert, Zossen (DE); Brigitte Lange, Berlin (DE); Regina Bienert, Rostok (DE)

(73) Assignee: Symrise AG, Holzminden (DE)

( * ) Notice: Subject to any disclaimer, the term of this patent is extended or adjusted under 35 U.S.C. 154(b) by 0 days.

(21) Appl. No.: 14/115,706

(22) PCT Filed: May 9, 2012

(86) PCT No.: PCT/EP2012/058586
§ 371 (c)(1),
(2), (4) Date: Nov. 5, 2013

(87) PCT Pub. No.: WO2012/152849
PCT Pub. Date: Nov. 15, 2012

(65) Prior Publication Data
US 2014/0066666 A1    Mar. 6, 2014

Related U.S. Application Data

(60) Provisional application No. 61/483,914, filed on May 9, 2011.

(51) Int. Cl.
*C07C 29/17* (2006.01)
*C07C 29/145* (2006.01)
*C07C 29/80* (2006.01)

(52) U.S. Cl.
CPC ............. *C07C 29/175* (2013.01); *C07C 29/145* (2013.01); *C07C 29/172* (2013.01); *C07C 29/80* (2013.01)

USPC .......................................... 568/865; 568/862

(58) Field of Classification Search
None
See application file for complete search history.

(56) References Cited

U.S. PATENT DOCUMENTS

| | | | | |
|---|---|---|---|---|
| 2,082,025 | A | * | 6/1937 | Peters, Jr. ...................... 549/429 |
| 2,201,347 | A | | 5/1940 | Rittmeister |
| 2,768,979 | A | * | 10/1956 | Robertson et al. ............ 568/865 |
| 3,083,236 | A | * | 3/1963 | Utne et al. ..................... 568/865 |
| 5,905,159 | A | * | 5/1999 | Fischer et al. ................ 549/429 |
| 6,528,665 | B1 | | 3/2003 | Cheng et al. |

FOREIGN PATENT DOCUMENTS

| | | |
|---|---|---|
| DE | 555405 C | 7/1932 |
| DE | 746307 C | 12/1944 |
| DE | 827804 C | 1/1952 |
| EP | 0141775 A1 | 5/1985 |
| EP | 0257243 A2 | 3/1988 |
| EP | 0655904 A1 | 6/1995 |
| EP | 1478231 A1 | 11/2004 |
| EP | 1876162 A1 | 1/2008 |
| WO | 2008151269 A2 | 12/2008 |

OTHER PUBLICATIONS

International Search Report and Written Opinion dated Aug. 22, 2012 for priority application PCT/EP2012/058586.
Wenjie Xu et al., "Direct catalytic conversion of furfural to 1,5-pentanediol by hydrogenolysis of the furan ring under mild conditions over Pt/CO2AlO4 catalyst," Chem. Commun., vol. 47, pp. 3924-3926, XP-002681491, Apr. 7, 2011, Royal Society of Chemistry.

* cited by examiner

*Primary Examiner* — Brian J Davis
(74) *Attorney, Agent, or Firm* — Novak Druce Connolly Bove + Quigg LLP

(57) ABSTRACT

A process for the preparation of 1,2-pentanediol by reaction of a starting material comprising one or both compounds from the group consisting of furfuryl alcohol and furfural with hydrogen in the presence of a first heterogeneous catalyst is described.

54 Claims, No Drawings

METHOD FOR PRODUCING 1,2-PENTANEDIOL

CROSS-REFERENCE TO RELATED APPLICATIONS

This application is a National Stage of International Application No. PCT/EP2012/058586, filed 9 May 2012, which claims the benefit under 35 U.S.C. §119(e) of U.S. Provisional Application No. 61/483,914, filed 9 May 2011, each of which is incorporated by reference in its entirety.

The present invention relates to a process for the preparation of 1,2-pentanediol (1,2-n-pentanediol) by reaction of a starting material comprising one or both compounds from the group consisting of furfuryl alcohol and furfural with hydrogen in the presence of a first heterogeneous catalyst. Such processes also include processes for the preparation of 1,2-pentanediol (1,2-n-pentanediol) from furfuryl alcohol and hydrogen in the presence of a heterogeneous platinum catalyst comprising (i) platinum and/or one or more platinum compounds and (ii) one or more support materials.

In the cosmetics field, 1,2-pentanediol is used, for example, inter alia as a skin moisturizing agent (EP 0 655 904) or as an antimicrobial agent (EP 1 478 231).

1,2-Pentanediol protects the skin from drying out due to environmental influences and the effects of the weather and is an important active ingredient in cosmetic formulations.

One of the requirements made of the quality of 1,2-pentanediol, in particular for use in the cosmetics field, is an odor that is as neutral as possible. An unpleasant or troublesome odor is caused by the other substances accompanying the 1,2-pentanediol, because 1,2-pentanediol in pure form is largely or completely odorless.

Depending on the preparation process, the crude product obtained in a particular case comprises, in addition to the desired 1,2-pentanediol, various secondary products, which have a more or less strong and in some cases very unpleasant smell.

These compounds having an undesirable smell can be partially removed or avoided to only an inadequate extent within the context of a subsequent purification process or by complex additional process steps.

U.S. Pat. No. 6,528,665 B1 proposes a process for the preparation of alkanediols that are as pure as possible. According to U.S. Pat. No. 6,528,665 B1, a purification is carried out at the stage of the epoxyalkanes, before they are hydrolyzed to the corresponding alkanediols.

EP 1 876 162 A1 describes the preparation of alkanediols from the corresponding olefins by means of epoxidation and subsequent hydrolysis. The crude products so obtained were purified further therein by means of subsequent treatment, in order to remove secondary products having an unpleasant smell.

The preparation of 1,2-pentanediol is nowadays generally carried out from n-pent-1-ene, which is (still) available from petrochemical sources. The n-pent-1-ene is reacted to give the corresponding epoxide with the aid of peroxides (e.g. hydrogen peroxide) and then converted into 1,2-pentanediol with organic acids such as formic acid or mineral acids.

This preparation method is described in EP 0 257 243 or EP 0 141 775 and has economic and ecological disadvantages. For example, the diester of 1,2-pentanediol that is formed as an intermediate in this process must be saponified in order to obtain 1,2-pentanediol. If the epoxidation of n-pent-1-ene is carried out, for example, with hydrogen peroxide and formic acid, sodium formate is formed as a coupling product in the subsequent saponification of the diformate of 1,2-pentanediol with sodium hydroxide solution and must be disposed of, thus contaminating the waste water, for example. Furthermore, n-pent-1-ene has a very low boiling point, which requires special and more expensive protective measures when handling and storing n-pent-1-ene owing to the risk of explosion that exists. In addition, it would be desirable to find a simple synthesis route that is practicable on an industrial scale, preferably without using a petrochemical raw material.

A substance that is obtainable from renewable raw materials is furfuryl alcohol. Furfuryl alcohol can be obtained in large amounts, for example, from sugar-containing cereal waste.

It is known from the literature that various compounds are formed in the hydrogenation or hydrogenolysis of furfuryl alcohol.

For example, Adkins and Connor [Journal of American Chemical Society 53, 1091 (1931)] report that the hydrogenation or hydrogenolysis of furfuryl alcohol at 175° C. in a liquid phase using copper chromite as catalyst yields a mixture of 40% 1,2-pentanediol, 30% 1,5-pentanediol, 10% amyl alcohol as well as 20% tetrahydrofurfuryl alcohol and methyltetrahydrofuran. Kaufmann and Adams [Journal of American Chemical Society 45, 3029 (1923)] report that the hydrogenolysis/hydrogenation of furfural in the presence of platinum black at room temperature yields a mixture of furfuryl alcohol, 1-pentanol, tetrahydrofurfuryl alcohol, 1,2-pentanediol and 1,5-pentanediol.

Furthermore, studies of catalytic hydrogenations or hydrogenolyses of furan and furan derivatives in the liquid phase by means of platinum dioxide catalysts are found in the works of Smith and Fuzek [Journal of American Chemical Society 71, 415 (1949)]. The reactions were carried out in acetic acid at a hydrogen pressure of 20, 40 or 60 psi (60 psi corresponds to about 4 bar), the mentioned catalyst was prepared according to the literature [Organic Synthesis 8, 92 (1928)]. In the hydrogenation or hydrogenolysis of furfuryl alcohol using platinum dioxide as catalyst, 1,2-pentanediol is allegedly formed in almost quantitative yield; the 1,2-pentanediol was separated from the acetic acid in the form of the diacetate.

Although this procedure for the preparation of 1,2-pentanediol has been reworked repeatedly in our own investigations, it was possible to obtain only a product mixture of tetrahydrofurfuryl alcohol, 2-methyltetrahydrofuran, 1-pentanol, 2-pentanol, 1,2-pentanediol and 1,5-pentanediol, the yield of 1,2-pentanediol being a maximum of 20% of the theoretical yield.

Accordingly, the object was, starting from furfuryl alcohol and/or furfural, to develop a process for the preparation of 1,2-pentanediol that is as effective and/or efficient as possible and also is preferably environmentally friendly and/or protective of resources.

It has now been found that the reaction of a starting material comprising one or both compounds from the group consisting of furfuryl alcohol and furfural with hydrogen in the presence of a heterogeneous catalyst comprising (i) one or more metals from the group consisting of platinum, rhodium, ruthenium, nickel, palladium and iridium in metallic form and/or one or more compounds of metals from the group consisting of platinum, rhodium, ruthenium, nickel, palladium and iridium, and (ii) one or more support materials yields the desired 1,2-pentanediol in a good yield and/or with good selectivity.

It has been found in particular that the hydrogenolysis of furfuryl alcohol in the presence of a heterogeneous platinum catalyst yields the desired 1,2-pentanediol in a good yield and/or with good selectivity when the heterogeneous platinum catalyst comprises (i) platinum and/or one or more platinum compounds and (ii) one or more support materials. This is the case in particular when the hydrogenolysis is carried out in specific diluents.

Accordingly, the present invention provides a process for the preparation of 1,2-pentanediol, comprising the step reaction of a starting material comprising one or both compounds from the group consisting of furfuryl alcohol and furfural with hydrogen in the presence of a first heterogeneous catalyst to form a mixture comprising 1,2-pentanediol and optionally one or more compounds from the group consisting of 1-hydroxy-2-pentanone, furfuryl alcohol and furfural, wherein the first heterogeneous catalyst (i) comprises one or more metals from the group consisting of platinum, rhodium, ruthenium, nickel, palladium and iridium in metallic form and/or one or more compounds of metals from the group consisting of platinum, rhodium, ruthenium, nickel, palladium and iridium, and (ii) one or more support materials.

Preferably, the first heterogeneous catalyst comprises (i) platinum in metallic form and/or one or more platinum (IV) compounds. Particularly preferably, the first heterogeneous catalyst is selected from the group consisting of catalysts comprising (i) platinum in metallic form and (ii) activated carbon, in particular platinum on activated carbon, catalysts comprising (i) platinum in metallic form and (ii) aluminum oxide, in particular platinum on aluminum oxide, catalysts comprising (i) platinum in metallic form and (ii) silicon dioxide, in particular platinum on silicon dioxide, catalysts comprising (i) platinum in metallic form and (ii) silicon carbide, in particular platinum on silicon carbide, catalysts comprising (i) platinum (IV) oxide and (ii) aluminum oxide, in particular platinum dioxide on aluminum oxide.

Preferably, the first heterogeneous catalysts to be used according to the invention are not catalysts that contain, in addition to a support material, two ingredients and are selected from the following list:

activated carbon/Pt/$ReO_2$,
MgO/Pd/$MnO_2$,
$Al_2O_3$/Rh/$MoO_3$,
aO/Ru/$Co_3O_4$,
amorphous aluminosilicate/Co/$TiO_2$,
$SiO_2$/Ni/$WO_3$,
CeO/PtRh/$Cr_2O_3$,
CaO/NiPd/$Fe_3O_4$,
MgO—$Al_2O_3$/RuFe/$V_2O_5$,
MgO/Pt/$ReO_2$,
$Al_2O_3$/Pd/$MnO_2$,
BaO/Rh/$MoO_3$,
amorphous aluminosilicate/Ru/$Co_3O_4$,
$SiO_2$/Co/$TiO_2$,
CeO/Ni/$WO_3$,
CoO/Pd/$Cr_2O_3$,
$Fe_2O_3$/Rh/$Fe_3O_4$,
$MnO_2$/Ru/$V_2O_5$.

Preferably, the first heterogeneous catalysts to be used according to the invention are not catalysts in which the following pairs of ingredients are present:

Pt/$ReO_2$, Pd/$MnO_2$, Rh/$MoO_3$, Ru/$Co_3O_4$, Co/$TiO_2$, Ni/$WO_3$, PtRh/$Cr_2O_3$, NiPd/$Fe_3O_4$, RuFe/$V_2O_5$, Pd/$Cr_2O_3$, Rh/$Fe_3O_4$, Ru/$V_2O_5$.

If constituent (i) of the first heterogeneous catalyst consists of platinum, then the first heterogeneous catalyst is preferably free of $ReO_2$ and free of $Cr_2O_3$, preferably free of rhenium and free of chromium. This preferably also applies to first heterogeneous catalysts whose constituent (i) comprises platinum.

If constituent (i) of the first heterogeneous catalyst consists of palladium, then the first heterogeneous catalyst is preferably free of $Fe_3O_4$ and free of $MnO_2$ and free of $Cr_2O_3$, preferably free of iron and free of manganese and free of chromium. This preferably also applies to first heterogeneous catalysts whose constituent (i) comprises palladium.

If constituent (i) of the first heterogeneous catalyst consists of rhodium, then the first heterogeneous catalyst is preferably free of $MoO_3$ and free of $Fe_2O_3$ and free of $Fe_3O_4$ and free of $Cr_2O_3$, preferably free of molybdenum and free of iron and free of chromium. This preferably also applies to first heterogeneous catalysts whose constituent (i) comprises palladium.

If constituent (i) of the first heterogeneous catalyst consists of ruthenium, then the first heterogeneous catalyst is preferably free of $Co_3O_4$ and free of $V_2O_5$, preferably free of cobalt and free of vanadium. This preferably also applies to first heterogeneous catalysts whose constituent (i) comprises ruthenium.

If constituent (i) of the first heterogeneous catalyst consists of nickel, then the first heterogeneous catalyst is preferably free of $WO_3$ and free of $Fe_3O_4$, preferably free of tungsten and iron. This preferably also applies to first heterogeneous catalysts whose constituent (i) comprises nickel.

Preferably, a first heterogeneous catalyst to be used according to the invention is free of oxides of the elements Re, Mo, Mn, Co, Ti, W, Cr, Fe, V and Ta.

In the first heterogeneous catalyst, the total concentration of (i) platinum, rhodium, ruthenium, nickel, palladium and iridium in metallic form and in the form of platinum, rhodium, ruthenium, nickel, palladium and iridium contained in compounds of those metals is preferably in the range from 0.1 wt. % to 50 wt. %, preferably from 0.5 wt. % to 20 wt. %, more preferably from 1 to 10 wt. %, particularly preferably from 1 wt. % to 5 wt. %, based on the total weight of all the constituents of the first heterogeneous catalyst.

The total concentration of (i) platinum, rhodium, ruthenium, nickel, palladium and iridium in metallic form and in the form of platinum, rhodium, ruthenium, nickel, palladium and iridium contained in compounds of those metals in the first heterogeneous catalyst is preferably in the range from 0.01 to 10 mol %, preferably in the range from 0.05 to 5 mol %, more preferably in the range from 0.1 to 2 mol %, based on the total amount of furfuryl alcohol and furfural that is used.

Preferably, both the total concentration, based on the total weight of all the constituents of the first heterogeneous catalyst, of (i) platinum, rhodium, ruthenium, nickel, palladium and iridium in metallic form and in the form of platinum, rhodium, ruthenium, nickel, palladium and iridium contained in compounds of those metals, and the total concentration, based on the total amount of furfuryl alcohol and furfural that is used, of (i) platinum, rhodium, ruthenium, nickel, palladium and iridium in metallic form and in the form of platinum, rhodium, ruthenium, nickel, palladium and iridium contained in compounds of those metals in the first heterogeneous catalyst are in the preferred ranges mentioned above.

For the reaction according to the invention in the presence of the first heterogeneous catalyst, molecular hydrogen is to be metered in an at least equimolar amount. However, it has been found to be more advantageous to meter in hydrogen in an excess. Therefore, in the reaction in the presence of the first heterogeneous catalyst, the molar ratio between hydrogen and the total amount of furfuryl alcohol and furfural is 1:1 or more and is preferably in the range from 4:1 to 100:1, particularly preferably in the range from 5:1 to 20:1.

In the reaction in the presence of the first heterogeneous catalyst, the hydrogen partial pressure is preferably in the range from 1 bar to 20 bar, preferably in the range from 1 bar to 8 bar, more preferably in the range from 1 bar to 4 bar.

The reaction in the presence of the first heterogeneous catalyst takes place in a liquid phase or in a gas phase.

If the reaction in the presence of the first heterogeneous catalyst is carried out in a gas phase, this preferably takes place at a temperature in the range from 100° C. to 250° C., more preferably in the range from 150° C. to 240° C., particularly preferably in the range from 170° C. to 230° C. The temperature and the hydrogen partial pressure are preferably in the preferred ranges mentioned above.

The reaction in the presence of the first heterogeneous catalyst preferably takes place in a reactor through which a gas stream flows continuously. On entering the reactor, the gas stream comprises the starting material (as described above) as well as hydrogen and optionally an inert gas, wherein
  the flow rate of the gas stream, based on the volume of the first heterogeneous catalyst (gas hourly space velocity GHSV), is from 500 $h^{-1}$ to 5000 $h^{-1}$, preferably from 900 $h^{-1}$ to 3600 $h^{-1}$
and/or
  the total concentration of furfuryl alcohol and furfural in the gas stream entering the reactor is from 1 mol % to 15 mol %, preferably from 3 mol % to 10 mol %.

Preferably, both the condition relating to the flow velocity and the condition relating to the total concentration of furfuryl alcohol and furfural in the gas stream entering the reactor are fulfilled.

The apparatus used for the reaction in the presence of the first heterogeneous catalyst in a gas phase is preferably a tubular reactor which is charged with a first heterogeneous catalyst as defined above. The feed stream, which is fed to the tubular reactor by way of suitable metering devices, consists of a starting material comprising one or both compounds from the group consisting of furfuryl alcohol and furfural and the necessary amount of hydrogen (preferably in the above-indicated molar ratio between hydrogen and the total amount of furfuryl alcohol and furfural) and optionally an inert gas. Furfuryl alcohol and/or furfural are converted into the gas phase by means of a saturator, which heats the liquid furfuryl alcohol and/or furfural to a temperature in the range from 80 to 120° C., particularly preferably from 90 to 110° C., and through which hydrogen or hydrogen and an inert gas flows. Alternatively, the liquid starting material is fed in by way of a metering pump or similar devices and an evaporator.

If the reaction in the presence of the first heterogeneous catalyst is carried out in a liquid phase, then it preferably takes place at a temperature in the range from −20° C. to +100° C., preferably from −20° C. to +50° C., more preferably in the range from −5 to +50° C., yet more preferably in the range from −5° C. to +30° C., particularly preferably in the range from 0° C. to +30° C., most particularly preferably in the range from 0° C. to +10° C. Preferably, the temperature and the hydrogen partial pressure are in the preferred ranges mentioned above.

The reaction time for the reaction in the presence of the first heterogeneous catalyst as defined above is preferably in the range from 1 to 20 hours, preferably in the range from 2 to 12 hours, more preferably in the range from 3 to 8 hours.

According to the invention, the reaction of furfuryl alcohol with hydrogen is preferably carried out in one or more, preferably organic diluents having a $pK_s$ value at 25° C. of greater than or equal to 6, preferably having a $pK_s$ value at 25° C. of greater than or equal to 8, preferably having a $pK_s$ value at 25° C. of greater than or equal to 10, particularly preferably having a $pK_s$ value at 25° C. of greater than or equal to 12.

Preference is further given to organic diluents having a $pK_s$ value at 25° C. in the range from 12 to 25, particularly preferably in the range from 13 to 20, most preferably in the range from 14 to 18.

The $pK_s$ value (also $pK_a$ value) corresponds to the negative common logarithm of the acid constant $K_s$. Acetic acid has a $pK_s$ value of 4.75.

The diluents to be used according to the invention are preferably inert under the reaction conditions, that is to say the diluents preferably do not themselves react, in particular are not themselves reduced, under the prevailing hydrogenation or hydrogenolysis conditions.

Diluents that are preferably to be used are or comprise one or more alcohols having from 1 to 4 carbon atoms, preferably selected from the group consisting of methanol, ethanol, n-propanol, isopropanol and mixtures thereof.

It is also possible to use non-polar and/or aprotic, inert solvents such as dibutyl ether, methyl tert-butyl ether (MTBE), cyclohexane, n-octane, isooctane or decalin, optionally in combination with one or more of the alcohols having from 1 to 4 carbon atoms characterized above as being preferred.

In a preferred embodiment, an inorganic acid, preferably having a $pK_s$ value at 25° C. of less than 3, preferably having a $pK_s$ value at 25° C. of less than 0, can be used in addition to a diluent, preferably in addition to one of the diluents characterized above as being preferred. A preferred inorganic acid is sulfuric acid, because it has been found to be particularly advantageous for the course of the hydrogenolysis in the process according to the invention.

In a particularly preferred embodiment, the reaction of furfuryl alcohol takes place in a diluent comprising or consisting of one or more alcohols selected from the group consisting of methanol, ethanol, n-propanol, isopropanol and mixtures thereof, and sulfuric acid. The combination of ethanol and sulfuric acid is particularly preferred.

If an inorganic acid is used, preferably sulfuric acid, the total amount is preferably in the range from 0.0001 to 1 wt. %, preferably in the range from 0.001 to 0.5 wt. %, particularly preferably in the range from 0.01 to 0.1 wt. %, based on the total mass of the diluent or diluents, the diluents in turn preferably being selected from the group consisting of methanol, ethanol, n-propanol, isopropanol and mixtures thereof.

The total amount of diluent or diluents, preferably having a $pK_s$ value at 25° C. characterized above as being preferred or particularly preferred, preferably selected from the group of the diluents characterized above as being preferred, is preferably in the range from 25 to 1000 wt. %, preferably in the range from 50 to 500 wt. %, more preferably in the range from 100 to 300 wt. %, based on the total amount of furfuryl alcohol used.

A first heterogeneous catalyst that is preferably to be used according to the invention is a heterogeneous platinum catalyst comprising (i) platinum and/or one or more platinum compounds (in particular platinum (IV) compounds) and (ii) one or more support materials. A heterogeneous platinum catalyst that is particularly preferably to be used according to the invention comprises (i) platinum and/or one or more platinum (IV) compounds and (ii) one or more support materials.

Preferred platinum (IV) compounds are $H_2PtCl_6$ and salts thereof, preferably $(NH_4)_2PtCl_6$, as well as platinum dioxide (of which $PtO_2$ and $PtO_2$ hydrate are preferred). A particularly preferred platinum (IV) compound is platinum dioxide $PtO_2$.

Preference is given to elemental, that is to say metallic, platinum, which can be doped with iron, vanadium and/or ruthenium.

The support material is preferably solid at 25° C. and 1013 mbar, preferably also under hydrogenation conditions. The support material is preferably selected from the group consisting of activated carbon, silica, silicon dioxide and/or aluminum oxide.

Particularly preferred support materials are aluminum oxide and activated carbon, because platinum catalysts to be used according to the invention comprising aluminum oxide and/or activated carbon produced the best yields and the best selectivities of 1,2-pentanediol.

Preferably, therefore, the support material comprises activated carbon and/or aluminum oxide, consists of aluminum oxide or consists of activated carbon.

Gamma-aluminum oxide has been found to be a particularly good support material.

Particularly good results in a process according to the invention were achieved with platinum dioxide on aluminum oxide, or platinum on activated carbon or aluminum oxide; the best results were achieved with platinum dioxide on aluminum oxide, in particular with platinum dioxide on gamma-aluminum oxide.

The heterogeneous platinum catalysts to be used according to the invention are known per se and can be obtained, for example, according to Anal. Chem. 1956, 28(3), 362-365 or Thermochimica Acta 1977, 20(3), 297-308 or Proceedings of the 13th International Conference On X-Ray Absorption Fine Structure (XAFS13), Stanford, Calif., 2006, edited by B. Hedman and P. Pianetta, eConf C060709 (2006) (the complete text is available at http://www.slac.stanford.edu/econf/C060709/papers/207_WEPO17.PDF) or analogously thereto.

The amount of the heterogeneous platinum catalyst is preferably in the range from 0.1 to 20 wt. %, preferably in the range from 0.25 to 15 wt. %, more preferably in the range from 0.5 to 12 wt. %, based on the amount of furfuryl alcohol used.

The amount of constituent (i) of the heterogeneous platinum catalyst, that is to say the total content of platinum and/or platinum compounds, is preferably in the range from 0.5 to 50 wt. %, preferably in the range from 0.5 to 20 wt. %, more preferably in the range from 0.5 to 10 wt. %, based on the total amount of the heterogeneous platinum catalyst.

Particularly preferred platinum catalysts in a process according to the invention are platinum dioxide on aluminum oxide, preferably platinum dioxide on gamma-aluminum oxide, and/or platinum on activated carbon, the total content of platinum dioxide and/or platinum being in the range from 0.5 to 10 wt. %, based on the total amount of heterogeneous platinum catalyst used.

Preferably, a platinum catalyst (as defined above) to be used according to the invention as the first heterogeneous catalyst is free of $ReO_2$ and free of $Cr_2O_3$, preferably free of rhenium and free of chromium. Preferably, a platinum catalyst (as defined above) to be used according to the invention as the first heterogeneous catalyst is free of $CeO_2$, preferably free of cerium oxides, more preferably free of cerium, rhenium and chromium. Preferably, a platinum catalyst (as defined above) to be used according to the invention as the first heterogeneous catalyst is free of oxides of the elements Re, Mo, Mn, Co, Ti, W, Cr, Fe, V and Ta.

In a preferred variant of the process according to the invention with a heterogeneous platinum catalyst as defined above, the mass ratio of furfuryl alcohol to the total amount of constituent (i) of the heterogeneous platinum catalyst is preferably in the range from 2000:1 to 10:1, preferably in the range from 1000:1 to 25:1, more preferably in the range from 500:1 to 50:1, most preferably in the range from 300:1 to 100:1.

Preferably, the hydrogenolysis of furfuryl alcohol in the process according to the invention is carried out at a temperature in the range from -20° C. to +50° C., preferably in the range from -5 to +30° C., more preferably in the range from 0 to +10° C.

The hydrogen pressure in the preferred variant of the process according to the invention with a heterogeneous platinum catalyst as defined above is preferably in the range from 1 to 20 bar, preferably in the range from 1 to 8 bar, more preferably in the range from 1 to 4 bar.

The reaction time in the preferred variant of the process according to the invention with a heterogeneous platinum catalyst as defined above is preferably in the range from 1 to 20 hours, preferably in the range from 2 to 12 hours, more preferably in the range from 3 to 8 hours.

The process according to the invention yields a product mixture in which 1,2-pentanediol generally represents the main product.

The reaction scheme below illustrates the reaction of furfuryl alcohol in a process according to the invention to give the desired main product 1,2-pentanediol and the secondary products that are generally obtained.

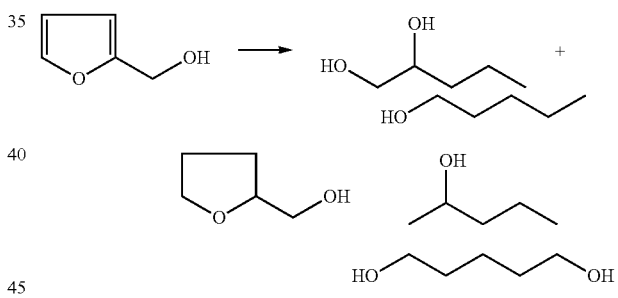

In addition to the secondary products shown in the reaction scheme, which, thanks to the good yield and/or good selectivity of the process according to the invention, are formed in only small amounts, 1-hydroxy-2-pentanone is formed in particular in addition to the target product 1,2-pentanediol. In an advantageous further development of the process according to the invention (see below), the 1-hydroxy-2-pentanone is likewise reacted in a further reaction step to form the target product 1,2-pentanediol.

Preferably, the reaction is conducted in such a manner that at least 80 wt. %, preferably at least 90 wt. %, more preferably at least 95 wt. %, of the furfuryl alcohol used is reacted.

Preferably, the reaction is conducted in such a manner that the reaction mixture present when the reaction is complete comprises at least 40 wt. % 1,2-pentanediol, preferably at least 50 wt. %, more preferably at least 60 wt. %, particularly preferably at least 70 wt. %, based on the total amount of products formed.

To clarify: the indicated amounts by weight of 1,2-pentanediol in the reaction mixture are based only on the total amount of products formed from furfuryl alcohol. Accordingly, when determining the above-indicated amounts by weight of 1,2-pentanediol, any amounts of unreacted furfuryl alcohol present in the reaction mixture when the reaction is complete, and the amounts of platinum catalyst(s) and diluent(s), are not to be taken into consideration.

The above-indicated amounts by weight of 1,2-pentanediol in the reaction mixture are based in particular on the total amount of 1-pentanediol, 2-pentanediol, tetrahydrofurfurol, 1,2-pentanediol and 1,5-pentanediol in the reaction mixture when the reaction of furfuryl alcohol is complete.

The process according to the invention can be carried out in the liquid phase or in the gas phase.

The reaction can be carried out continuously, semi-continuously or batchwise.

The reaction is preferably carried out in a batch process, preferably in a reaction vessel, the furfuryl alcohol and preferably the diluent that is optionally used being present in the liquid phase and being mixed with the catalyst to be used according to the invention.

The reaction is preferably carried out in a reaction tube, the catalyst to be used according to the invention being in the form of a fixed bed and the furfuryl alcohol and preferably the diluent that is optionally used being present in the liquid phase and being brought into contact with the fixed catalyst bed.

The process according to the invention for the preparation of 1,2-pentanediol by reaction of furfuryl alcohol in the presence of a heterogeneous platinum catalyst is preferably characterized by the following steps:
(a) provision of a starting material comprising one or both compounds from the group consisting of furfuryl alcohol and furfural;
(b) provision of a first heterogeneous catalyst as defined above;
(c) optional provision of one or more diluents;
(d) preparation of a mixture comprising the components provided in steps (a) and (b) and optionally (c), and contacting of the mixture with hydrogen
or
(d') preparation of a mixture comprising the starting material provided in step (a) and hydrogen and optionally an inert gas, and contacting of the mixture with the first heterogeneous catalyst provided according to step (b);
(e) in the mixture prepared in step (d) or (d'), reaction of the starting material with hydrogen in the presence of the first heterogeneous catalyst to form a mixture comprising 1,2-pentanediol and optionally one or more compounds from the group consisting of 1-hydroxy-2-pentanone, furfuryl alcohol and furfural;
(f) optional separation of the 1,2-pentanediol by distillation.

The diluents indicated above as being preferred or particularly preferred are thereby correspondingly preferred or particularly preferred.

The first heterogeneous catalysts indicated above as being preferred or particularly preferred are thereby correspondingly preferred or particularly preferred.

Preferably one, a plurality or all of the reaction conditions indicated above as being preferred or particularly preferred are thereby established.

The order in which the components provided in steps (a) to (c) are mixed together in step (d) is not important.

In a particularly preferred variant, the process according to the invention comprises the steps:
(a) provision of furfuryl alcohol,
(b) provision of at least a first heterogeneous catalyst as defined above, preferably a heterogeneous platinum catalyst, which comprises (i) platinum and/or a platinum compound and (ii) one or more support materials,
(c) optional provision of one or more diluents, preferably having a $pK_s$ value at 25° C. of greater than or equal to 6,
(d) preparation of a mixture comprising the components provided in steps (a) and (b) and preferably (c),
(e) contacting of the mixture prepared in step (d) with hydrogen.

In an alternative preferred variant, the process according to the invention comprises the steps:
(a) provision of a starting material comprising one or both compounds from the group consisting of furfuryl alcohol and furfural,
(b) provision of a first heterogeneous catalyst as defined above,
(d') preparation of a mixture comprising the starting material provided in step (a) and hydrogen and optionally an inert gas, and contacting of the mixture with the first heterogeneous catalyst provided according to step (b),
(e) in the mixture prepared in step (d'), reaction of the starting material with hydrogen in the presence of the first heterogeneous catalyst to form a mixture comprising 1,2-pentanediol and optionally one or more compounds from the group consisting of 1-hydroxy-2-pentanone, furfuryl alcohol and furfural.

With the process according to the invention described above it is possible, by reaction of a starting material comprising one or both compounds from the group consisting of furfuryl alcohol and furfural, to achieve yields of 1,2-pentanediol that are superior to the known prior art. A further advantageous feature of the process according to the invention is the formation of the secondary product 1-hydroxy-2-pentanone with a high yield and selectivity. By contrast, other secondary products which are typically formed in processes known from the prior art are formed in only very small amounts in the process according to the invention. In particular, cyclic compounds can scarcely be detected in the mixture obtainable by the process according to the invention.

The sum of the selectivities for 1-hydroxy-2-pentanone and 1,2-pentanediol is generally over 80%, even in the case of almost complete conversion. In tests of processes known from the prior art for the preparation of 1,2-pentanediol, the compound 1-hydroxy-2-pentanone was not detected as a secondary product. The formation of 1-hydroxy-2-pentanone is advantageous compared with other secondary products because 1-hydroxy-2-pentanone can readily and very selectively be hydrogenated to 1,2-pentanediol under suitable conditions, in the presence of a second heterogeneous catalyst. This is the subject of an advantageous further development of the process according to the invention, which is described hereinbelow.

In an advantageous further development, the process according to the invention, in particular in the preferred variants described above, therefore comprises the further step
reaction of compounds from the group consisting of 1-hydroxy-2-pentanone, furfuryl alcohol and furfural from the mixture formed in the above-described reaction in the presence of the first heterogeneous catalyst with hydrogen in the presence of a second heterogeneous catalyst to form 1,2-pentanediol,
wherein the second heterogeneous catalyst comprises
(i') one or more metals from the group consisting of platinum, rhodium, ruthenium, nickel, palladium and iridium in metallic form and/or one or more compounds of metals from the group consisting of platinum, rhodium, ruthenium, nickel, palladium and iridium, and (ii') one or more support materials.

With this advantageous further development of the process according to the invention, the overall selectivity for 1,2-pentanediol can be increased to more than 80%. Separation of the 1,2-pentanediol before the reaction in the presence of the second heterogeneous catalyst is not necessary.

In the second heterogeneous catalyst, the total concentration of platinum, rhodium, ruthenium, nickel, palladium and iridium in metallic form and in the form of platinum, rhodium, ruthenium, nickel, palladium and iridium contained in compounds of those metals is preferably in the range from 0.1 wt. % to 20 wt. %, preferably from 0.5 wt. % to 10 wt. %, based on the total weight of all the constituents of the second heterogeneous catalyst.

In a preferred variant of this advantageous further development of the process according to the invention, the first and second heterogeneous catalysts have the same composition.

Preferably, the support material (ii) of the first heterogeneous catalyst and/or the support material (ii') of the second heterogeneous catalyst is solid at 25° C. and 1013 mbar, preferably also at 230° C. and 1013 mbar, the support material (ii) and/or the support material (ii') preferably being selected from the group consisting of activated carbon, silica, silicon dioxide, silicon carbide, aluminum oxide, zirconium dioxide, titanium dioxide, niobium trioxide, cerium dioxide and mixtures thereof.

The reaction in the presence of the second heterogeneous catalyst takes place in a liquid phase or in a gas phase.

If the reaction in the presence of the second heterogeneous catalyst is carried out in a gas phase, then the temperature is preferably in the range from 25° C. to 240° C., particularly preferably in the range from 100° C. to 130° C., and/or the hydrogen partial pressure is in the range from 1 bar to 10 bar. Preferably, the temperature and the hydrogen partial pressure are in the preferred ranges mentioned here.

Preferably, the reaction in the presence of the second heterogeneous catalyst takes place in a reactor through which a gas stream flows continuously. On entering the reactor, the gas stream comprises the mixture formed in the reaction in the presence of the first heterogeneous catalyst (as described above) as well as hydrogen and optionally an inert gas, wherein the flow rate of the gas stream, based on the volume of the second heterogeneous catalyst (gas hourly space velocity GHSV), is from $500\ h^{-1}$ to $5000\ h^{-1}$, preferably from $900\ h^{-1}$ to $3600\ h^{-1}$ and/or the total concentration of 1-hydroxy-2-pentanone, furfuryl alcohol and furfural in the gas stream entering the reactor is from 1 mol % to 15 mol %, preferably from 3 mol % to 10 mol %.

Preferably, both the condition relating to the flow velocity and the condition relating to the total concentration of 1-hydroxy-2-pentanone, furfuryl alcohol and furfural in the gas stream entering the reactor are fulfilled.

In a preferred variant of the process according to the invention, both the reaction in the presence of the first heterogeneous catalyst and the reaction in the presence of the second heterogeneous catalyst are carried out in the gas phase. This variant has the advantage that no diluents (solvents) are required, which represents a considerable economic and ecological advantage. For this variant of the process according to the invention there is preferably used an apparatus comprising a first reaction tube and a second reaction tube, which is connected downstream of the first reaction tube. The first heterogeneous catalyst is disposed in the first reaction tube, and the second heterogeneous catalyst is disposed in the second reaction tube. It is thereby possible to set a different temperature in the first reaction tube than in the second reaction tube.

If the reaction in the presence of the second heterogeneous catalyst is carried out in a liquid phase, then the temperature is in the range from −20° C. to +150° C., preferably from −20° C. to +50° C., more preferably in the range from −5 to +50° C., yet more preferably in the range from −5° C. to +30° C., particularly preferably in the range from 0° C. to +30° C., most particularly preferably in the range from 0° C. to +10° C., and/or the hydrogen partial pressure is in the range from 1 bar to 100 bar, preferably in the range from 1 bar to 50 bar, more preferably in the range from 1 bar to 20 bar. Preferably, the temperature and the hydrogen partial pressure are in the preferred ranges mentioned here.

Preferably, the liquid phase comprises one or more, preferably polar diluents, the diluent or diluents preferably being selected from the group consisting of water, alcohols having from 1 to 4 carbon atom, ethers selected from the group consisting of aliphatic ethers, oligomeric terminally hydroxy-functionalised ethers and cyclic ethers, and mixtures thereof. The diluents to be used according to the invention are preferably inert under the hydrogenation conditions, that is to say the diluents preferably do not themselves react, in particular are not themselves reduced, under the prevailing hydrogenation conditions.

Alcohols having from 1 to 4 carbon atoms that are preferably to be used as diluents are selected from the group consisting of methanol, ethanol, n-propanol, isopropanol, n-butanol, isobutanol, tert-butanol. Preferred ethers to be used as diluents are selected from the group consisting of aliphatic ethers such as methyl tert-butyl ether, oligomeric terminally hydroxy-functionalised ethers such as diethylene glycol and triethylene glycol, cyclic ethers such as tetrahydrofuran and dioxane, or mixtures thereof.

A stirrer vessel reactor is preferably used as the apparatus for the reaction in the presence of the second heterogeneous catalyst. The reaction time for the reaction in the presence of the second heterogeneous catalyst in the stirrer vessel reactor is preferably in the range from 0.25 to 20 hours, preferably in the range from 2 to 12 hours, more preferably in the range from 3 to 8 hours.

In a particularly preferred variant of the process according to the invention, the reaction of a starting material comprising one or both compounds from the group consisting of furfuryl alcohol and furfural in the presence of a first heterogeneous catalyst takes place in a gas phase, and the reaction of compounds from the group consisting of 1-hydroxy-2-pentanone, furfuryl alcohol and furfural from the mixture formed in the presence of the first heterogeneous catalyst with hydrogen in the presence of a second heterogeneous catalyst takes place in a liquid phase. To that end, the organic components of the mixture formed in the presence of the first heterogeneous catalyst are condensed (i.e. converted into the liquid phase) in a suitable apparatus. The resulting condensate is then transferred to a reactor, preferably a stirrer vessel reactor, for carrying out the reaction in the presence of the second heterogeneous catalyst. Preferably, the reaction conditions established in this procedure for the reaction in the presence of the first heterogeneous catalyst are such that almost complete conversion of the starting compound furfuryl alcohol or furfural is achieved.

One or more diluents are preferably added to the condensate that forms, the total amount of diluents added to the condensate preferably being in the range from 25 to 1000 wt. %, preferably in the range from 50 to 500 wt. %, more preferably in the range from 100 to 300 wt. %, based on the mass of the condensate.

The total concentration of (i) platinum, rhodium, ruthenium, nickel, palladium and iridium in metallic form and in the form of platinum, rhodium, ruthenium, nickel, palladium and iridium contained in compounds of those metals in the second heterogeneous catalyst is preferably in the range from 0.01 to 10 mol %, based on the amount of 1-hydroxy-2-pentanone contained in the condensate.

The process according to the invention according to the advantageous further development described above is preferably characterized by the following steps:
(a) provision of a starting material comprising one or both compounds from the group consisting of furfuryl alcohol and furfural,
(b) provision of a first heterogeneous catalyst as defined above,
(c) optional provision of one or more diluents,
(d) preparation of a mixture comprising the components provided in steps (a) and (b) and optionally (c), and contacting of the mixture with hydrogen
or
(d') preparation of a mixture comprising the starting material provided in step (a) and hydrogen and optionally an inert gas, and contacting of the mixture with the first heterogeneous catalyst provided according to step (b),
(e) in the mixture prepared in step (d) or (d'), reaction of the starting material with hydrogen in the presence of the first heterogeneous catalyst to form a mixture comprising 1,2-pentanediol and one or more compounds from the group consisting of 1-hydroxy-2-pentanone, furfuryl alcohol and furfural,
(f) provision of a second heterogeneous catalyst as defined above,
(g) optional provision of one or more diluents,
(h) optional condensation of organic components of the mixture formed in step (e), and preparation of a mixture comprising the mixture formed in step (e), or organic components condensed therefrom, and the components provided in steps (f) and optionally (g), and contacting of the mixture with hydrogen
or
(h') contacting of the mixture formed in step (e), in the presence of hydrogen and optionally an inert gas, with the second heterogeneous catalyst provided according to step (f),
(i) reaction of compounds from the group consisting of 1-hydroxy-2-pentanone, furfuryl alcohol and furfural from the mixture formed in step (e) with hydrogen in the presence of the second heterogeneous catalyst to form 1,2-pentanediol,
(j) optional separation of the 1,2-pentanediol by distillation.

The diluents indicated above as being preferred or particularly preferred are thereby correspondingly preferred or particularly preferred.

The heterogeneous catalysts indicated above as being preferred or particularly preferred are thereby correspondingly preferred or particularly preferred.

Preferably one, a plurality or all of the reaction conditions indicated above as being preferred or particularly preferred are thereby established.

The order in which the components provided in steps (a) to (c) are mixed together in step (d) is not important.

In all the process variants according to the invention, unreacted hydrogen can very easily be separated from the organic constituents of the reaction mixture, for example in a condenser, and fed to the reaction in the presence of the first heterogeneous catalyst again.

In a first preferred variant, the process according to the invention comprises the steps:
(a) provision of a starting material comprising one or both compounds from the group consisting of furfuryl alcohol and furfural,
(b) provision of a first heterogeneous catalyst as defined above,
(d') preparation of a mixture comprising the starting material provided in step (a) and hydrogen and optionally an inert gas, and contacting of the mixture with the first heterogeneous catalyst provided according to step (b),
(e) in the mixture prepared in step (d'), reaction of the starting material with hydrogen in the presence of the first heterogeneous catalyst to form a mixture comprising 1,2-pentanediol and one or more compounds from the group consisting of 1-hydroxy-2-pentanone, furfuryl alcohol and furfural,
(f) provision of a second heterogeneous catalyst as defined above,
(h') contacting of the mixture formed in step (e), in the presence of hydrogen and optionally an inert gas, with the second heterogeneous catalyst provided according to step (f),
(i) reaction of compounds from the group consisting of 1-hydroxy-2-pentanone, furfuryl alcohol and furfural from the mixture formed in step (e) with hydrogen in the presence of the second heterogeneous catalyst to form 1,2-pentanediol,
(j) optional separation of the 1,2-pentanediol by distillation.

In a second preferred variant, the process according to the invention comprises the steps:
(a) provision of a starting material comprising one or both compounds from the group consisting of furfuryl alcohol and furfural,
(b) provision of a first heterogeneous catalyst as defined above,
(c) optional provision of one or more diluents,
(d) preparation of a mixture comprising the components provided in steps (a) and (b) and optionally (c), and contacting of the mixture with hydrogen,
(e) in the mixture prepared in step (d), reaction of the starting material with hydrogen in the presence of the first heterogeneous catalyst to form a mixture comprising 1,2-pentanediol and one or more compounds from the group consisting of 1-hydroxy-2-pentanone, furfuryl alcohol and furfural,
(f) provision of a second heterogeneous catalyst as defined above,
(g) optional provision of one or more diluents,
(h) preparation of a mixture comprising the mixture formed in step (e) and the components provided in steps (f) and optionally (g), and contacting of the mixture with hydrogen,
(i) reaction of compounds from the group consisting of 1-hydroxy-2-pentanone, furfuryl alcohol and furfural from the mixture formed in step (e) with hydrogen in the presence of the second heterogeneous catalyst to form 1,2-pentanediol,
(j) optional separation of the 1,2-pentanediol by distillation.

In a third preferred variant, the process according to the invention comprises the steps:
(a) provision of a starting material comprising one or both compounds from the group consisting of furfuryl alcohol and furfural, (b) provision of a first heterogeneous catalyst as defined above,
(d') preparation of a mixture comprising the starting material provided in step (a) and hydrogen and optionally an inert gas, and contacting of the mixture with the first heterogeneous catalyst provided according to step (b),
(e) in the mixture prepared in step (d'), reaction of the starting material with hydrogen in the presence of the first heterogeneous catalyst to form a mixture comprising 1,2-pentanediol and one or more compounds from the group consisting of 1-hydroxy-2-pentanone, furfuryl alcohol and furfural,
(f) provision of a second heterogeneous catalyst as defined above,
(g) optional provision of one or more diluents,
(h) condensation of organic components of the mixture formed in step (e), and preparation of a mixture comprising (h') contacting of the mixture formed in step (e), in the presence of hydrogen and optionally an inert gas, with the second heterogeneous catalyst provided according to step (f),
(i) reaction of compounds from the group consisting of 1-hydroxy-2-pentanone, furfuryl alcohol and furfural from the mixture formed in step (e) with hydrogen in the presence of the second heterogeneous catalyst to form 1,2-pentanediol,
(j) optional separation of the 1,2-pentanediol by distillation.

The process according to the invention, in particular in its preferred variants and the advantageous further development described above, yields a product mixture in which 1,2-pentanediol generally represents the main product.

The reaction scheme below illustrates the reaction of furfural or furfuryl alcohol in a process according to the invention by way of the intermediate 1-hydroxy-2-pentanone to give the desired main product 1,2-pentanediol and the secondary products generally obtained thereby.

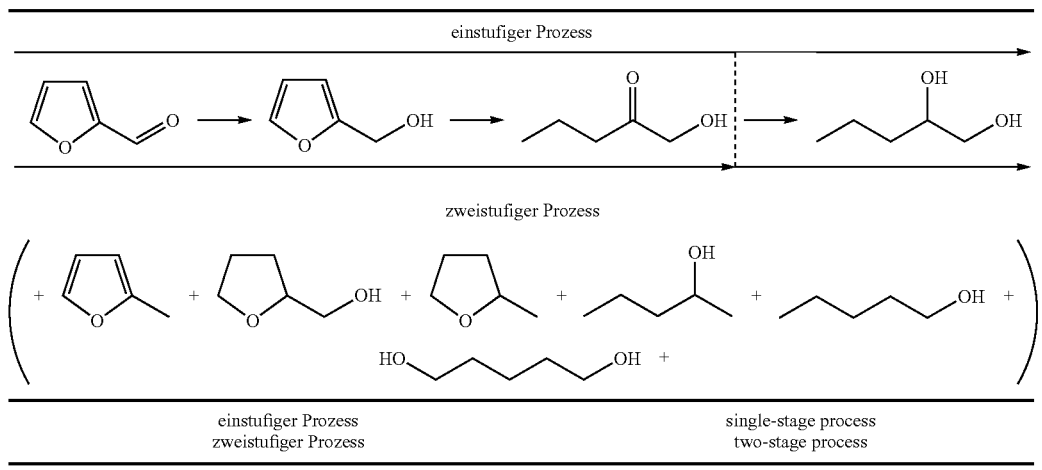

organic components condensed from the mixture formed in step (e) and the components provided in steps (f) and optionally (g), and contacting of the mixture with hydrogen,
(i) reaction of compounds from the group consisting of 1-hydroxy-2-pentanone, furfuryl alcohol and furfural from the mixture formed in step (e) with hydrogen in the presence of the second heterogeneous catalyst to form 1,2-pentanediol,
(j) optional separation of the 1,2-pentanediol by distillation.

In a fourth preferred variant, the process according to the invention comprises the steps:
(a) provision of a starting material comprising one or both compounds from the group consisting of furfuryl alcohol and furfural,
(b) provision of a first heterogeneous catalyst as defined above,
(c) optional provision of one or more diluents,
(d) preparation of a mixture comprising the components provided in steps (a) and (b) and optionally (c), and contacting of the mixture with hydrogen,
(e) in the mixture prepared in step (d) or (d'), reaction of the starting material with hydrogen in the presence of the first heterogeneous catalyst to form a mixture comprising 1,2-pentanediol and one or more compounds from the group consisting of 1-hydroxy-2-pentanone, furfuryl alcohol and furfural,
(f) provision of a second heterogeneous catalyst as defined above, If furfural is used as the starting material, it is first converted into furfuryl alcohol.

If the process according to the invention is carried out as a single-stage process (comprising a reaction step in the presence of a first heterogeneous catalyst as described above but not a further reaction step in the presence of a second heterogeneous catalyst as described above), then there are formed, in addition to the target product 1,2-pentanediol, the secondary products indicated in brackets in the lower part of the scheme, as well as 1-hydroxy-2-pentanone. This variant is symbolized in the above scheme by the continuous arrow labeled "single-stage process".

If the process according to the invention is carried out according to the advantageous further development as a two-stage process (comprising a reaction step in the presence of a first heterogeneous catalyst as described above and a further reaction step in the presence of a second heterogeneous catalyst as described above), then there are formed, in addition to the target product 1,2-pentanediol, the secondary products indicated in brackets in the lower part of the scheme, while 1-hydroxy-2-pentanone formed in the reaction in the presence of the first heterogeneous catalyst is largely converted into 1,2-pentanediol in the reaction in the presence of the second heterogeneous catalyst. This variant is symbolized in the above scheme by the two-part arrow labeled "two-stage process".

Preferably, the reaction is conducted in such a manner that at least 80 wt. %, preferably at least 90 wt. %, more preferably at least 95 wt. %, of the furfural and/or furfuryl alcohol used is reacted.

Preferably, the reaction is conducted in such a manner that the reaction mixture present after the single-or two-stage process comprises at least 30 wt. % 1,2-pentanediol, preferably at least 50 wt. %, more preferably at least 70 wt. %, particularly preferably at least 80 wt. %, based on the total amount of products formed. The amounts Y of 1,2-pentanediol or 1-hydroxy-2-pentanone in the reaction mixture are based on the total amount of the products formed from furfuryl alcohol or furfural. Accordingly, when determining the amount Y of 1,2-pentanediol, any amounts of unreacted furfuryl alcohol or furfural still present in the reaction mixture when the reaction is complete, and the amounts of catalyst(s) and diluent(s), are not to be taken into consideration. The amounts Y of 1,2-pentanediol or 1-hydroxy-2-pentanone in the reaction mixture are based in particular on the total amount of 1-pentanol, 2-pentanol, pentane, tetrahydrofurfuryl alcohol, 1-hydroxy-2-pentanone, methylfuran, methyltetrahydrofuran, 1,2-pentanediol and 1,5-pentanediol in the reaction mixture when the reaction is complete.

The present invention relates also to the use of a heterogeneous catalyst comprising (i) one or more metals from the group consisting of platinum, rhodium, ruthenium, nickel, palladium and iridium in metallic form and/or one or more compounds of metals from the group consisting of platinum, rhodium, ruthenium, nickel, palladium and iridium,
and
(ii) one or more support materials for the hydrogenolysis of a starting material comprising one or more compounds from the group consisting of furfuryl alcohol, furfural and 1-hydroxy-2-pentanone or for the reaction of a starting material comprising one or more compounds from the group consisting of furfuryl alcohol, furfural and 1-hydroxy-2-pentanone to give a hydrogenated product.

With regard to preferred embodiments and preferred use conditions of the catalyst to be used according to the invention, reference is made to the above statements.

The invention relates further to the use of a platinum catalyst comprising (i) platinum and/or one or more platinum compounds and (ii) one or more support materials for the hydrogenolysis of furfuryl alcohol.

The invention relates in particular to the use of a platinum catalyst selected from the group consisting of platinum on activated carbon, platinum on aluminum oxide and platinum dioxide on aluminum oxide for the hydrogenolysis of furfuryl alcohol.

The 1,2-pentanediol obtained by the process according to the invention can, if required, be purified further by subsequent simple steps, for example by means of distillation or rectification. It is then largely or completely colorless and largely or completely odorless and—also because of the quality in terms of odor—suitable for use in cosmetics.

In the examples which follow, all amounts are by weight, unless indicated otherwise.

EXAMPLE 1

According to the Invention 100 g (1.02 mol) of furfuryl alcohol were dissolved in 200 g of ethanol; 10 g of catalyst (5 wt. % platinum dioxide on gamma-aluminum oxide, corresponding to 0.5 g of platinum dioxide) were added, and hydrogenation was carried out at 0 to 5° C. and a hydrogen pressure of 1 bar. After 5 hours, the absorption of hydrogen was complete. The catalyst was filtered off, and the solvent ethanol and finally the product mixture were distilled off. There were obtained 105 g of a distillate having the following composition:

2% 2-pentanediol
2% 1-pentanediol
15% tetrahydrofurfurol
80% 1,2-pentanediol
1% 1,5-pentanediol Yield: 84 g (0.81 mol) of 1,2-pentanediol (corresponding to 80% of the theoretical yield).

The distillates from six hydrogenation batches were combined (630 g in total) and subjected to fractional distillation on a 1 m packed column. 475 g of colorless 1,2-pentanediol having a purity of 99.9% were obtained as the main fraction.

The resulting 1,2-pentanediol was colorless and odorless.

The heterogeneous platinum catalyst used in Example 1 was prepared by dissolving 1.8 g of hexachloroplatinic acid in water and applying the solution to 10 g of the support material gamma-aluminum oxide by means of an incipient-wetness process. The solid so obtained was introduced at a temperature in the range from 310 to 320° C. into a NaNO$_3$ melt, the temperature of the resulting mixture was increased gradually to 500° C., and the mixture was then maintained at 500° C. for one hour.

EXAMPLE 2

Comparison Example I

In accordance with Journal of American Chemical Society 71, 415 (1949) or the literature reference cited therein Journal of American Chemical Society 67, 272 (1945), 100 g (1.02 mol) of furfuryl alcohol were dissolved in 200 g of acetic acid; 4 g of platinum dioxide (without support material; supplier: Acros) were added, and hydrogenation was carried out at 0 to 5° C. and a hydrogen pressure of 1 bar. After 10 hours, the absorption of hydrogen was complete, the catalyst was filtered off, and the solvent was distilled off. The distillation residue was then taken up in 500 g of methyl tert-butyl ether and stirred with 40 g (0.74 mol) of sodium methylate in order to deacetylate the diols present in the form of mono-or di-acetate. After addition of 50 g of water, the mixture was neutralized with semi-concentrated hydrochloric acid, the phases were separated, and the solvent was removed. After distillation, there were obtained 80 g of an oily liquid having the following composition:

26% 2-pentanediol
10% 1-pentanediol
35% tetrahydrofurfurol
26% 1,2-pentanediol
2% 1,5-pentanediol Yield: 21 g (0.20 mol) of 1,2-pentanediol (corresponding to 20% of the theoretical yield).

EXAMPLE 3

Comparison Example II

In accordance with Journal of American Chemical Society 67, 272 (1945), 5 g (0.05 mol) of furfuryl alcohol were dissolved in 50 ml of acetic acid; 0.2 g of platinum dioxide was added, and hydrogenation was carried out at 20 to 25° C. and a hydrogen pressure of 1 bar.

The result corresponded to that of Example 2 (Comparison Example I).

EXAMPLES 4-7

According to the Invention 3 g of a granulated heterogeneous catalyst comprising (i) platinum and (ii) $Al_2O_3$ were disposed in the tubular reactor of a continuous gas-phase apparatus. The concentration of (i) platinum is 10 wt. %, based on the total weight of all the constituents of the catalyst. The apparatus comprises a saturator filled with furfuryl alcohol (FA), inlet pipes for hydrogen and an inert gas, gas metering units, a tubular reactor and a condensation unit.

The volume flow of furfuryl alcohol was controlled via the temperature of the saturator and the metering of the hydrogen stream and optionally an additional inert gas stream. The gaseous mixture comprising furfuryl alcohol and hydrogen was passed through the tubular reactor, and organic components as well as water from the product gas stream were converted into the liquid state of aggregation in a condensation unit. Samples were taken at regular intervals and the composition of the condensate was analyzed by means of various analytical methods. The reaction conditions and the conversion X based on furfuryl alcohol and the contents Y (as defined above) of 1-hydroxy-2-pentanone and 1,2-pentanediol in the total amount of the products formed from furfuryl alcohol are given in Table 1.

EXAMPLE 8

According to the Invention

The test arrangement of Examples 4-7 was used, 3 g of a heterogeneous catalyst comprising (i) platinum and (ii) $Al_2O_3$ being disposed in the tubular reactor. The concentration of (i) platinum is 5 wt. %, based on the total weight of all the constituents of the catalyst. The further procedure corresponds to Examples 4-7. The reaction conditions and the conversion X based on furfuryl alcohol and the contents Y (as defined above) of 1-hydroxy-2-pentanone and 1,2-pentanediol in the total amount of the products formed from furfuryl alcohol are given in Table 1.

EXAMPLE 9

According to the Invention 0.5 g of a condensate from a reaction in the gas phase as described above was reacted for 4 hours at room temperature under 5 bar $H_2$ in 25 ml of ethanol in the presence of a catalyst comprising (i) platinum and (ii) $Al_2O_3$. The condensate comprised 0.1% furfuryl alcohol, 35% 1,2-pentanediol and 36% 1-hydroxy-2-pentanone. The concentration of (i) platinum is 10 wt. % based on the total weight of all the constituents of the catalyst and 2 mol % based on the amount of 1-hydroxy-2-pentanone in the condensate.

The composition of the reaction mixture was determined by means of gas chromatography/mass spectroscopy (GC/MS) after removal of the catalyst by filtration. The conversion X based on furfuryl alcohol and the contents Y (as defined above) of 1-hydroxy-2-pentanone and 1,2-pentanediol in the total amount of the products formed from furfuryl alcohol are given in Table 2.

EXAMPLE 10

According to the Invention 0.5 g of a condensate from a reaction in the gas phase as described above was reacted for 4 hours at room temperature under 20 bar $H_2$ in 25 ml of ethanol in the presence of a catalyst comprising (i) rhodium and (ii) $Al_2O_3$. The condensate comprised 0.1% furfuryl alcohol, 35% 1,2-pentanediol and 36% 1-hydroxy-2-pentanone. The concentration of (i) rhodium is 5 wt. % based on the total weight of all the constituents of the catalyst and 2 mol % based on the amount of 1-hydroxy-2-pentanone in the condensate.

The composition of the reaction mixture was determined by means of GC/MS after removal of the catalyst by filtration. The conversion X based on furfuryl alcohol and the contents Y (as defined above) of 1-hydroxy-2-pentanone and 1,2-pentanediol in the total amount of the products formed from furfuryl alcohol are given in Table 2.

TABLE 1

| Example No. | Flow FA [g/h] | $C_{FA}$ in the gas stream [mol %] | $T_{sat}$ [° C.] | $T_{react}$ [° C.] | $H_2$ flow [mln/min] | Sampling time [min] | X FA [%]* | Y 1,2-PD [%]* | Y 1-Hydroxy-2-pentanone [%]* |
|---|---|---|---|---|---|---|---|---|---|
| 4 | 0.619 | 3.78 | 90 | 230 | 60 | 123 | 98.3 | 38.0 | 54 |
| 5 | 0.268 | 3.29 | 90 | 230 | 30 | 119 | 99.8 | 47.0 | 51 |
| 6 | 0.450 | 1.87 | 110 | 230 | 30/ 2 bar $H_2$ over-pressure | 303 | 99.5 | 60.9 | 17.8 |
| 7 | 0.159 | 1.98 | 110 | 190 | 30/ 4 bar $H_2$ over-pressure | 295 | 99.9 | 69.7 | 3.0 |
| 8 | 0.387 | 4.68 | 90 | 220 | 30 | 331 | 99.6 | 37.9 | 40.1 |

*The percentages are based on amounts of substance.

TABLE 2

| Example No. | X FA [%]* | Y 1,2-PD [%]* | Y 1-Hydroxy-2-pentanone [%]* |
|---|---|---|---|
| 9 | 100 | 49 | 14 |
| 10 | 100 | 44 | 14 |

*The percentages are based on amounts of substance.

EXAMPLE 11

According to the Invention 0.5 g of 1-hydroxy-2-pentanone (94%) was reacted for 4 hours at room temperature under 5 bar $H_2$ in 25 ml of ethanol in the presence of a catalyst comprising (i) platinum and (ii) $Al_2O_3$. The concentration of (i) platinum is 10 wt. % based on the total weight of all the constituents of the catalyst and 2 mol % based on the amount of 1-hydroxy-2-pentanone.

The composition of the reaction mixture was determined by means of GC/MS after separation of the catalyst. The conversion X based on 1-hydroxy-2-pentanone and the content Y of 1,2-pentanediol in the total amount of the products formed from 1-hydroxy-2-pentanone are given in Table 3.

EXAMPLE 12

According to the Invention 0.5 g of 1-hydroxy-2-pentanone (94%) was reacted for 4 hours at room temperature under 5 bar $H_2$ in 25 ml of ethanol in the presence of a catalyst comprising (i) platinum and (ii) $Al_2O_3$. The concentration of (i) platinum is 1 wt. % based on the total weight of all the constituents of the catalyst and 2 mol % based on the amount of 1-hydroxy-2-pentanone.

The composition of the reaction mixture was determined by means of GC/MS after separation of the catalyst. The conversion X based on 1-hydroxy-2-pentanone and the content Y of 1,2-pentanediol in the total amount of the products formed from 1-hydroxy-2-pentanone are given in Table 3.

EXAMPLE 13

According to the Invention 0.5 g of 1-hydroxy-2-pentanone (94%) was reacted for 6 hours at room temperature under 50 bar $H_2$ in 25 ml of ethanol in the presence of a catalyst comprising (i) ruthenium and (ii) $Al_2O_3$. The concentration of (i) ruthenium is 5 wt. % based on the total weight of all the constituents of the catalyst and 2 mol % based on the amount of 1-hydroxy-2-pentanone.

The composition of the reaction mixture was determined by means of GC/MS after separation of the catalyst. The conversion X based on 1-hydroxy-2-pentanone and the content Y of 1,2-pentanediol in the total amount of the products formed from 1-hydroxy-2-pentanone are given in Table 3.

TABLE 3

| Example No. | X 1-Hydroxy-2-pentanone [%]* | Y 1,2-PD [%]* |
|---|---|---|
| 11 | 69 | 69 |
| 12 | 99 | 80 |
| 13 | 98 | 96 |

*The percentages are based on amounts of substance.

The invention claimed is:

1. A process for the preparation of 1,2-pentanediol, comprising reacting a starting material comprising one or both compounds selected from the group consisting of furfuryl alcohol and furfural with hydrogen in the presence of a first heterogeneous catalyst to form a mixture comprising 1,2-pentanediol and optionally one or more compounds selected from the group consisting of 1-hydroxy-2-pentanone, furfuryl alcohol and furfural, wherein the first heterogeneous catalyst comprises:
    one or more metals selected from the group consisting of platinum, rhodium, ruthenium, nickel, palladium and iridium in metallic form and/or one or more compounds of metals selected from the group consisting of platinum, rhodium, ruthenium, nickel, palladium and iridium; and
    one or more support materials selected from the group consisting of activated carbon, aluminum oxide, silicon dioxide, and silicon carbide.

2. The process according to claim 1, wherein the first heterogeneous catalyst comprises platinum in metallic form and/or one or more platinum (IV) compounds.

3. The process according to a claim 1, wherein in the first heterogeneous catalyst, the total concentration of the one or more metals and/or one or more compounds of metals is in the range from 0.1 wt. % to 50 wt. %, based on the total weight of all the constituents of the first heterogeneous catalyst.

4. The process according to claim 1, wherein in the reaction in the presence of the first heterogeneous catalyst the hydrogen partial pressure is in the range from 1 bar to 20 bar.

5. The process according to claim 1, wherein in the reaction in the presence of the first heterogeneous catalyst the molar ratio between hydrogen and the total amount of furfuryl alcohol and furfural is 1:1 or more.

6. The process according claim 1, wherein the reaction in the presence of the first heterogeneous catalyst takes place in a gas phase.

7. The process according to claim 6, wherein the reaction in the presence of the first heterogeneous catalyst takes place in a reactor through which a gas stream flows continuously, which gas stream, on entering the reactor, comprises said starting material, hydrogen and optionally an inert gas;
    wherein the flow rate of the gas stream, based on the volume of the first heterogeneous catalyst (gas hourly space velocity GHSV), is from 500 $h^{-1}$ to 5000 $h^{-1}$.

8. The process according to claim 1, wherein the reaction in the presence of the first heterogeneous catalyst takes place in a liquid phase.

9. The process according to claim 8, wherein the liquid phase comprises one or more organic diluents having a pKs value at 25° C. of greater than or equal to 6.

10. The process according to claim 1, wherein the first heterogeneous catalyst comprises platinum (IV) oxide; and wherein one of the at least one or more support materials is aluminum oxide.

11. The process according to claim 1, wherein in the first heterogeneous catalyst, the total concentration of the one or more metals and/or one or more compounds of metals is in the range from 1 wt. % to 5 wt. %, based on the total weight of all the constituents of the first heterogeneous catalyst.

12. The process according to claim 1, wherein the amount of the first heterogeneous Catalyst is in the range from 0.1 to 20 wt. % based on the amount of furfuryl alcohol; and wherein the first heterogeneous catalyst comprises platinum in metallic form or one or more compounds of platinum.

13. The process according to claim 1, wherein the amount of the first heterogeneous catalyst is in the range from 0.5 to 12 wt. % based on the amount of furfuryl alcohol; and wherein the first heterogeneous catalyst comprises platinum in metallic form or one or more compounds of platinum.

14. The process according to claim 1, wherein in the first heterogeneous catalyst, the total concentration of the one or more metals and/or one or more compounds of metals is in the range from 0.01 to 10 mol %, based on the total amount of furfuryl alcohol and furfural used.

15. The process according to claim 1, wherein in the first heterogeneous catalyst, the total concentration of the one or more metals and/or one or more compounds of metals is in the range from 0.1 to 2 mol %, based on the total amount of furfuryl alcohol and furfural used.

16. The process according to claim 1, wherein in the reaction in the presence of the first heterogeneous catalyst the hydrogen partial pressure is in the range from 1 bar to 4 bar.

17. The process according to claim 1, wherein in the reaction in the presence of the first heterogeneous catalyst the molar ratio between hydrogen and the total amount of furfuryl alcohol and furfural is in the range from 5:1 to 20:1.

18. The process according to claim 1, wherein the reaction in the presence of the first heterogeneous catalyst takes place in a gas phase at a temperature in the range from 100° C. to 250° C.

19. The process according to claim 1, wherein the reaction in the presence of the first heterogeneous catalyst takes place in a gas phase at a temperature in the range from 170° C. to 230° C.

20. The process according to claim 1, wherein the reaction in the presence of the first heterogeneous catalyst takes place at a temperature in the range from −20° C. to +100° C.

21. The process according to claim 1, wherein the reaction in the presence of the first heterogeneous catalyst takes place at a temperature in the range from −0° C. to +10° C.

22. The process according to claim 6, wherein the reaction in the presence of the first heterogeneous catalyst takes place in a reactor through which a gas stream flows continuously, which gas stream, on entering the reactor, comprises said starting material, hydrogen and optionally an inert gas; wherein the flow rate of the gas stream, based on the volume of the first heterogeneous catalyst (gas hourly space velocity GHSV), is from 900 h$^{-1}$ to 3600 h$^{-1}$.

23. The process according to claim 6, wherein the reaction in the presence of the first heterogeneous catalyst takes place in a reactor through which a gas stream flows continuously, which gas stream, on entering the reactor, comprises said starting material, hydrogen and optionally an inert gas; wherein the total concentration of furfuryl alcohol and furfural in the gas stream entering the reactor is from 1 mol % to 15 mol %.

24. The process according to claim 6, wherein the reaction in the presence of the first heterogeneous catalyst takes place in a reactor through which a gas stream flows continuously, which gas stream, on entering the reactor, comprises said starting material, hydrogen and optionally an inert gas; wherein the total concentration of furfuryl alcohol and furfural in the gas stream entering the reactor is from 3 mol % to 10 mol %.

25. The process according to claim 8, wherein the liquid phase comprises one or more organic diluents having a pKs value at 25° C. of greater than or equal to 12.

26. The process according to claim 9, wherein one of the one or more organic diluents comprises one or more alcohols having from 1 to 4 carbon atoms.

27. The process according to claim 9, wherein one of the one or more organic diluents is selected from the group consisting of methanol, ethanol, n-propanol, isopropanol and mixtures thereof.

28. The process according to claim 9, wherein the total amount of diluents is in the range from 25 to 1000 wt. %, based on the total amount of furfuryl alcohol used.

29. The process according to claim 9, wherein the total amount of diluents is in the range from 100 to 300 wt. %, based on the total amount of furfuryl alcohol used.

30. The process according to claim 9, wherein the total amount of diluents is in the range from 25 to 1000 wt. %, based on the total amount of furfuryl alcohol and furfural used.

31. The process according to claim 9, wherein the total amount of diluents is in the range from 100 to 300 wt. %, based on the total amount of furfuryl alcohol and furfural used.

32. A process for the preparation of 1,2-pentanediol comprising:
  providing a starting material comprising one or both compounds selected from the group consisting of furfuryl alcohol and furfural;
  providing a first heterogeneous catalyst comprising: one or more metals selected from the group consisting of platinum, rhodium, ruthenium, nickel, palladium and iridium in metallic form and/or one or more compounds of metals selected from the group consisting of platinum, rhodium, ruthenium, nickel, palladium and iridium; and
  one or more first support materials selected from the group consisting of activated carbon, aluminum oxide, silicon dioxide, and silicon carbide; and
  forming a first mixture of the starting material, the first heterogeneous catalyst, and hydrogen, wherein in the first mixture, reaction of the starting material with hydrogen in the presence of the first heterogeneous catalyst forms a second mixture comprising 1,2-pentanediol and optionally one or more compounds selected from the group consisting of 1-hydroxy-2-pentanone, furfuryl alcohol and furfural.

33. The process according to claim 32, wherein forming the first mixture comprises: mixing the starting material and the first heterogeneous catalyst; and
  contacting the mixture of the starting material and the first heterogeneous catalyst with hydrogen.

34. The process according to claim 32, wherein forming the first mixture comprises:
  mixing the starting material and hydrogen; and
  contacting the mixture of the starting material hydrogen with the first heterogeneous catalyst.

35. The process according to claim 32 further comprising distilling the 1,2-pentanediol from the second mixture.

36. The process according to claim 32 further comprising reacting the second mixture with hydrogen in the presence of a second heterogeneous catalyst comprising: one or more metals selected from the group consisting of platinum, rhodium, ruthenium, nickel, palladium and iridium in metallic form and/or one or more compounds of metals selected from the group consisting of platinum, rhodium, ruthenium, nickel, palladium and iridium; and one or more second support materials.

37. The process according to claim 36, wherein at least one of the first support materials of the first heterogeneous catalyst is solid at 25° C. and 1013 mbar.

38. The process according to claim 36, wherein at least one of the first support materials of the first heterogeneous catalyst is solid at 230° C. and 1013 mbar.

39. The process according to claim 36, wherein at least one of the second support materials of the second heterogeneous catalyst is solid at 25° C. and 1013 mbar.

40. The process according to claim 36, wherein at least one of the second support materials of the second heterogeneous catalyst is solid at 230° C. and 1013 mbar.

41. The process according to claim 36, wherein at least one of the second support materials of the second heterogeneous catalyst is selected from the group consisting of activated carbon, silica, silicon dioxide, silicon carbide, aluminum oxide, zirconium dioxide, titanium dioxide, niobium trioxide, cerium dioxide and mixtures thereof.

42. The process according to claim 36, wherein the first and second heterogeneous catalysts have the same composition.

43. The process according to claim 36, wherein in the second heterogeneous catalyst, the total concentration of the one or more metals and/or one or more compounds of metals is in the range from 0.1 wt. % to 20 wt. % based on the total weight of all the constituents of the second heterogeneous catalyst.

44. The process according to claim 36, wherein the reaction in the presence of the second heterogeneous catalyst takes place in a gas phase.

45. The process according to claim 36, wherein the reaction in the presence of the second heterogeneous catalyst takes place in a gas phase at a temperature in the range from 25° C. to 240° C.

46. The process according to claim 36, wherein the reaction in the presence of the second heterogeneous catalyst takes place in a gas phase at a hydrogen partial pressure in the range from 1 bar to 10 bar.

47. The process according to claim 36, wherein the reaction in the presence of the second heterogeneous catalyst takes place in a reactor through which a gas stream flows continuously, wherein the gas stream, on entering the reactor, comprises the first mixture, hydrogen and optionally an inert gas; and wherein the flow rate of the gas stream, based on the volume of the second heterogeneous catalyst (gas hourly space velocity GHSV), is from 500 $h^{-1}$ to 5000 $h^{-1}$.

48. The process according to claim 36, wherein the reaction in the presence of the second heterogeneous catalyst takes place in a reactor through which a gas stream flows continuously, wherein the gas stream, on entering the reactor, comprises the first mixture, hydrogen and optionally an inert gas; and wherein total concentration of 1-hydroxy-2-pentanone, furfuryl alcohol and furfural in the gas stream entering the reactor is from 1 mol% to 15 mol %.

49. The process according to claim 36, wherein the reaction in the presence of the second heterogeneous catalyst takes place in a liquid phase.

50. The process according to claim 36, wherein the reaction in the presence of the second heterogeneous catalyst takes place in a liquid phase at a temperature in the range from −20° C. to +150° C.

51. The process according to claim 36, wherein the reaction in the presence of the second heterogeneous catalyst takes place in a liquid phase at a hydrogen partial pressure in the range from 1 bar to 100 bar.

52. The process according to claim 36, wherein the reaction in the presence of the second heterogeneous catalyst takes place in a liquid phase; and wherein the liquid phase comprises one or more diluents selected from the group consisting of water, alcohols having from 1 to 4 carbon atoms, ethers selected from the group consisting of aliphatic ethers, oligomeric terminally hydroxy-functionalised ethers and cyclic ethers, and mixtures thereof.

53. The process according to claim 52, wherein the reaction of the starting material comprising one or both compounds selected from the group consisting of furfuryl alcohol and furfural with hydrogen in the presence of the first heterogeneous catalyst to form the first mixture comprising 1,2-pentanediol and one or more compounds selected from the group consisting of 1-hydroxy-2-pentanone, furfuryl alcohol and furfural takes place in a gas phase;

wherein the first mixture formed is condensed;

wherein one or more of the diluents are added to the condensate that is formed; and wherein the total amount of the diluents added to the condensate is in the range from 25 to 1000 wt. % based on the mass of the condensate.

54. The process according to claim 53, wherein the total concentration of the one or more metals and/or one or more compounds of metals in the second heterogeneous catalyst is in the range from 0.01 to 10 mol %, based on the amount of 1-hydroxy-2-pentanone contained in the condensate.

* * * * *